(12) United States Patent
Jarvi et al.

(10) Patent No.: US 7,385,056 B2
(45) Date of Patent: Jun. 10, 2008

(54) SYNTHESIS OF HETEROARYL ACETAMIDES

(75) Inventors: Esa T. Jarvi, Ballwin, MO (US); Douglas C. Miller, University City, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 442 days.

(21) Appl. No.: 10/537,604

(22) PCT Filed: Dec. 16, 2003

(86) PCT No.: PCT/US03/39951

§ 371 (c)(1), (2), (4) Date: Jun. 3, 2005

(87) PCT Pub. No.: WO2004/058758

PCT Pub. Date: Jul. 15, 2004

(65) Prior Publication Data

US 2006/0025588 A1     Feb. 2, 2006

(51) Int. Cl.
| C07D 498/00 | (2006.01) |
| C07D 487/00 | (2006.01) |
| C07D 471/02 | (2006.01) |
| C07D 491/02 | (2006.01) |
| C07D 498/02 | (2006.01) |
| C07D 513/02 | (2006.01) |
| C07D 235/02 | (2006.01) |
| C07D 403/02 | (2006.01) |

(52) U.S. Cl. .................... 544/91; 544/281; 546/121; 548/303.1; 548/302.7

(58) Field of Classification Search ............ 544/91, 544/281; 546/121; 548/303.1, 302.7
See application file for complete search history.

(56) References Cited

U.S. PATENT DOCUMENTS

| 4,382,938 A | 5/1983 | Kaplan et al. |
| 4,675,323 A | 6/1987 | George et al. |
| 4,794,185 A | 12/1988 | Rossey et al. |
| 4,808,594 A * | 2/1989 | George et al. ............ 514/300 |
| 4,847,263 A * | 7/1989 | George et al. ............ 514/300 |
| 5,512,590 A | 4/1996 | George et al. |
| 6,281,360 B1 | 8/2001 | Ettema et al. |
| 6,384,226 B2 | 5/2002 | Castaldi |
| 6,861,525 B2 * | 3/2005 | Schloemer ................. 546/121 |
| 2007/0213537 A1* | 9/2007 | Jarvi et al. ................. 546/119 |

FOREIGN PATENT DOCUMENTS

| EP | 0 251 859 A2 | 1/1988 |
| FR | 2 593 179 | 1/1986 |
| FR | 2 700 546 | 1/1993 |
| FR | 2 741 073 | 11/1995 |
| WO | WO 00/08021 | 2/1900 |
| WO | WO 01/38327 A2 | 5/2001 |
| WO | WO 01/80857 A1 | 11/2001 |
| WO | WO 02/14306 A1 | 2/2002 |
| WO | WO 02/18303 A2 | 3/2002 |

OTHER PUBLICATIONS

Schmitt et al. "Imidazo[1,2-b]pyridazines. XXIII* Some 5-Deaza Analogues. Synthesis of Some 2-Aryl-6-(chloro, methoxy or unsubstituted)-3-(variously substituted)imidazo[1,2-a]pyridines and Their Affinity for Central and Mitochondrial Benzodiazepine Receptors", Aust. J. Chem., 1997, 50, 719-725.

* cited by examiner

Primary Examiner—D. Margaret Seaman
Assistant Examiner—Niloofar Rahmani

(57) ABSTRACT

An improved process for the preparation of a heteroaryl acetamide from a heteroaryl α-hydroxyacetamide is provied. The process comprises directly hydrogenating the heteroaryl α-hydroxyacetamide in the presence of a strong acid, a halide and a catalyst. In one embodiment, the heteroaryl acetamide is zolpidem and the heteroaryl α-hydroxyacetamide is α-hydroxyzolpidem.

21 Claims, No Drawings

SYNTHESIS OF HETEROARYL ACETAMIDES

BACKGROUND OF THE INVENTION

The present application is generally directed to a process for the synthesis of heteroaryl acetamides.

Various processes for the preparation of heteroaryl acetamides have been proposed. In general, they differ in the procedure used for the introduction of the acetamide chain.

In U.S. Pat. No. 4,794,185, Rossey et al. disclose a process of preparing an imidazopyridine acetamide by reacting an imidazopyridine with a dialkoxyalkylamide to produce an imidazopyridine α-hydroxyacetamide intermediate. The intermediate is then converted to an α-chloroacetamide and subsequently reduced to produce the desired imidazopyridine acetamide.

SUMMARY OF THE INVENTION

Among the various aspects of the present invention is a process for converting heteroaryl α-hydroxyacetamides directly to the corresponding heteroaryl acetamides. In one embodiment, the process comprises hydrogenating the heteroaryl α-hydroxyacetamide in the presence of a strong acid, a halide and a hydrogenation catalyst.

The present invention is further directed to a process for converting imidazopyridine α-hydroxyacetamides directly to the corresponding imidazopyridine acetamides. In this embodiment, an imidazopyridine α-hydroxyacetamide is hydrogenated in the presence of a strong acid, a halide and a hydrogenation catalyst.

In another embodiment, α-hydroxy zolpidem is hydrogenated in the presence of a strong acid, a halide and a hydrogenation catalyst to produce zolpidem.

DETAILED DESCRIPTION

Among the various aspects of the invention is a process for preparing heteroaryl acetamides which are biologically active, by directly hydrogenating heteroaryl α-hydroxyacetamides in the presence of a strong acid, a halide, and a catalyst.

In one embodiment, the starting heteroaryl α-hydroxyacetamide is represented by Formula 1 and the product heteroaryl acetamide is represented by Formula 1A.

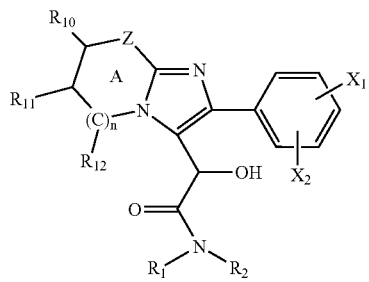

Formula 1

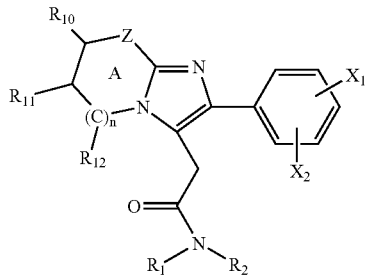

Formula 1A wherein

Z is O, $NR_{20}$ or $CR_{21}$;

$X_1$ and $X_2$ are independently selected from the group consisting of hydrogen, halogen, $C_{1-4}$ alkoxy, $C_{1-6}$ alkyl, $CF_3$ and $CH_3SO_2$;

$R_1$ and $R_2$ are independently hydrogen or $C_{1-5}$ alkyl;

$R_{10}$ is hydrogen, halogen, $C_{1-4}$ alkyl, or a member of a fused ring wherein the fused ring is (i) a substituted or unsubstituted, saturated or unsaturated, five or six-membered, heterocyclic or carbocyclic ring fused to the A ring comprising $R_{10}$, the carbon atom to which $R_{10}$ is attached, $R_{20}$, and the nitrogen atom to which $R_{20}$ is attached, or (ii) a six-membered, aromatic, carbocyclic ring fused to the A ring comprising $R_{10}$, $R_{11}$, and the carbon atoms to which $R_{10}$ and $R_{11}$ are attached, optionally substituted with Y at a substitutable position thereof;

$R_{11}$ is hydrogen, halogen, $C_{1-4}$ alkyl, or a member of a fused ring wherein the fused ring is (i) a six-membered, aromatic, carbocyclic ring fused to the A ring comprising $R_{10}$, $R_{11}$, and the carbon atoms to which $R_{10}$ and $R_{11}$ are attached, optionally substituted with Y at a substitutable position thereof, or (ii) a six-membered, aromatic, carbocyclic ring fused to the A ring comprising $R_{11}$, $R_{12}$ and the carbon atoms to which $R_{11}$ and $R_{12}$ are attached, optionally substituted with Y at a substitutable position thereof;

$R_{12}$, if present, is hydrogen, halogen, $C_{1-4}$ alkyl, or a member of a fused ring wherein the fused ring is (i) a six-membered, aromatic, carbocyclic ring fused to the A ring comprising $R_{11}$, $R_{12}$, and the carbon atoms to which $R_{11}$ and $R_{12}$ are attached, optionally substituted with Y at a substitutable position thereof;

$R_{20}$ is $C_{1-4}$ alkyl or a member of a fused ring wherein the fused ring is a substituted or unsubstituted, saturated or unsaturated, five or six-membered, heterocyclic or carbocyclic ring fused to the A ring comprising $R_{10}$, the carbon atom to which $R_{10}$ is attached, $R_{20}$, and the nitrogen atom to which $R_{20}$ is attached;

$R_{21}$ is hydrogen, halogen or $C_{1-4}$ alkyl;

n is 0 or 1;

each Y is independently hydrogen, halogen or $C_{1-4}$ alkyl; and when Z is $CR_{21}$, the A ring is aromatic.

In a further embodiment, the starting material and product of the process of the present invention have the structures of Formulae 1 and 1A, respectively, wherein Z is —$NR_{20}$, n is zero, $R_{20}$ and $R_{10}$ together with the atoms to which they are attached define a five-membered heterocyclic ring fused to the A ring, and $R_{10}$ and $R_{11}$ together with the atoms to which they are attached define a six-membered, aromatic carbocyclic ring fused to the A ring. In this embodiment, for example, the starting material and product may correspond to Formulae 2 and 2A, respectively,

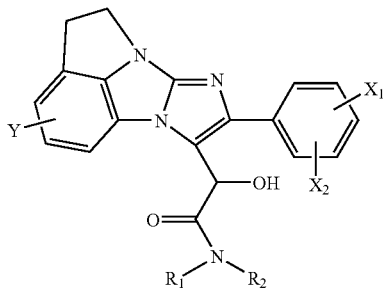

Formula 2

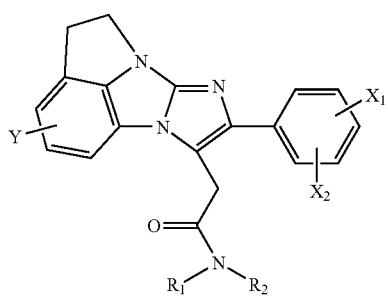

Formula 2A wherein $R_1$, $R_2$, $X_1$, $X_2$ and Y are as previously defined. In one preferred embodiment when the starting material and product correspond to Formulae 2 and 2A, $X_1$ and $X_2$ are independently hydrogen or halogen, $R_1$ and $R_2$ are independently hydrogen or $C_{1-5}$ alkyl, and Y is hydrogen, halogen or $C_{1-4}$ alkyl.

In another embodiment, the starting material and product of the process of the present invention have the structures of Formulae 1 and 1A wherein Z is —$NR_{20}$, n is zero, $R_{20}$ and $R_{10}$ together with the atoms to which they are attached define a six-membered heterocyclic ring fused to the A ring, and $R_{10}$ and $R_{11}$ together with the atoms to which they are attached define a six-membered, aromatic carbocyclic ring fused to the A ring. In this embodiment, for example, the starting material and product may correspond to Formulae 3 and 3A, respectively,

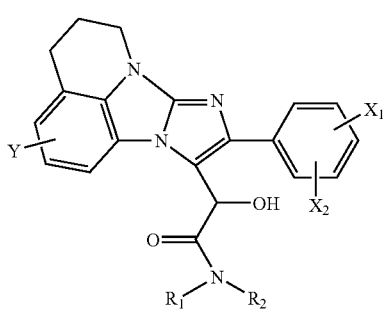

Formula 3

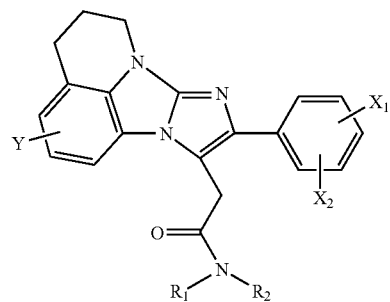

Formula 3A wherein $R_1$, $R_2$, $X_1$, $X_2$ and Y are as previously defined. In one preferred embodiment when the starting material and product correspond to Formulae 3 and 3A, $X_1$ and $X_2$ are independently hydrogen or halogen, $R_1$ and $R_2$ are independently hydrogen or $C_{1-5}$ alkyl and Y is hydrogen, halogen or $C_{1-4}$ alkyl.

In yet another embodiment, the starting material and product of the process of the present invention have the structures of Formulae 1 and 1A wherein Z is O, n is zero, $R_{10}$ and $R_{11}$ together with the atoms to which they are attached define a six-membered, aromatic carbocyclic ring fused to the A ring. In this embodiment, for example, the starting material and product may correspond to Formulae 4 and 4A, respectively,

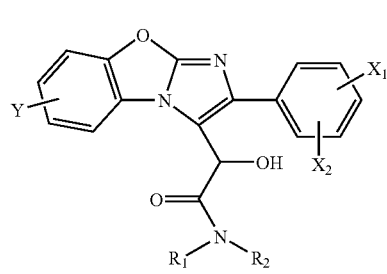

Formula 4

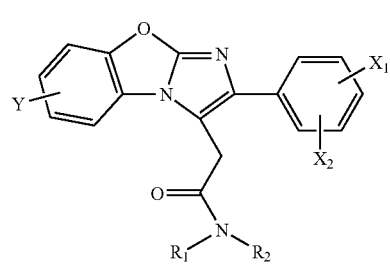

Formula 4A wherein $R_1$, $R_2$, $X_1$, $X_2$ and Y are as previously defined. In one preferred embodiment when the starting material and product correspond to Formulae 4 and 4A, $X_1$ and $X_2$ are independently hydrogen or halogen, $R_1$ and $R_2$ are independently hydrogen or $C_{1-5}$ alkyl and Y is hydrogen, halogen or $C_{1-4}$ alkyl.

In still another embodiment, the starting material and product of the process of the present invention have the structures of Formulae 1 and 1A wherein Z is $NR_{20}$, n is zero, $R_{10}$ and $R_{11}$ together with the atoms to which they are attached define a six-membered, aromatic carbocyclic ring fused to the A ring. In this embodiment, for example, the starting material and product may correspond to Formulae 5 and 5A, respectively,

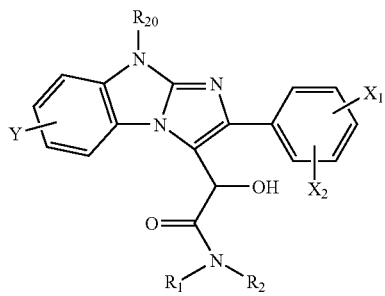

Formula 5

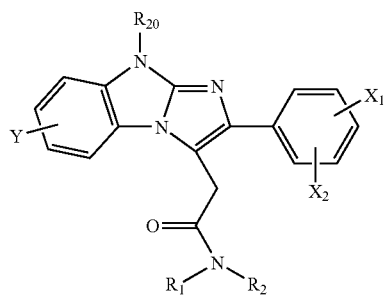

Formula 5A wherein $R_1$, $R_2$, $X_1$, $X_2$ and Y are as previously defined. In one preferred embodiment when the starting material and product correspond to Formulae 5 and 5A, $X_1$ and $X_2$ are independently hydrogen or halogen, $R_1$ and $R_2$ are independently hydrogen or $C_{1-5}$ alkyl and Y is hydrogen, halogen or $C_{1-4}$ alkyl.

In a further embodiment, the starting material and product of the process of the present invention have the structures of Formulae 1 and 1A wherein Z is $CR_{21}$, $R_{10}$, $R_{11}$, $R_{12}$, and $R_{21}$ are independently hydrogen, halogen or $C_{1-4}$ alkyl and n is 1. In this embodiment, for example, the starting material, a heteroaryl α-hydroxyacetamide, and product, a heteroaryl acetamide, may correspond to Formulae 6 and 6A, respectively,

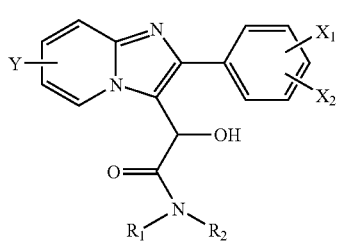

Formula 6

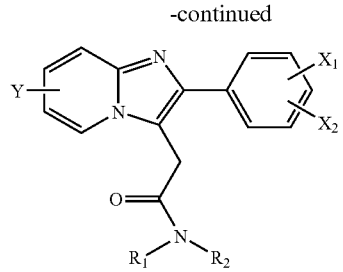

Formula 6A wherein
Y is hydrogen, halogen or $C_{1-4}$ alkyl;
$X_1$ and $X_2$ are independently selected from the group consisting of hydrogen, halogen, $C_{1-4}$ alkoxy, $C_{1-6}$ alkyl, $CF_3$ and $CH_3SO_2$; and
$R_1$ and $R_2$ are independently hydrogen or $C_{1-5}$ alkyl.

In another embodiment, the starting imidazopyridine α-hydroxyacetamide is represented by Formula 7 and the imidazopyridine acetamide product is represented by Formula 7A,

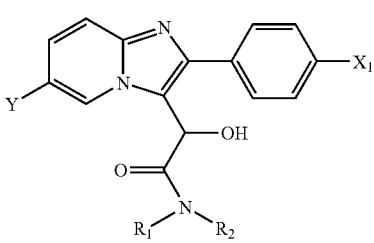

Formula 7

Formula 7A wherein Y, $X_1$, $R_1$ and $R_2$ are $C_{1-4}$ alkyl. In another embodiment, Y, $X_1$, $R_1$ and $R_2$ are methyl; the compound with these values for formula 7 is known as α-hydroxyzolpidem (AHZ).

The heteroaryl α-hydroxyacetamides of Formulae 1-5 may be prepared by reaction of the appropriate fused ring imidazo derivative with glyoxylic acid to produce an α-hydroxy acid which is subsequently acetylated, transformed into the α-acetoxy acetamide via an imidazolide and deacetylated to produce an α-hydroxy acetamide. This process is described in more detail in U.S. Pat. No. 4,675,323 and FR 2593179.

The imidazopyridine α-hydroxyacetamides of Formulae 2-4 and 6-7, generally, may be prepared by reaction of the appropriate imidazo derivative with N,N-dimethyl-2,2-dimethoxyacetamide or N,N-dimethyl-2,2-diethoxyacetamide to produce the imidazo α-hydroxyacetamide used as the starting material in the present invention. This process is described in more detail in U.S. Pat. Nos. 4,794,185, 5,512,590, WO 00/08021, FR 2700546 and FR 2741073.

In general, each of the products, i.e., the compounds of Formulae 1A-7A may be formed by the direct hydrogenation of the compounds of Formulae 1-7 respectively, in the presence of hydrogen gas, a strong acid, a halide and a hydrogenation catalyst.

The hydrogenation catalyst is typically a solid catalyst in whatever form is suitable and effective for achieving the hydrogenation reactions of the invention. In one embodiment, the catalyst is a precious metal catalyst. For example, the catalyst may be a platinum, palladium, ruthenium, osmium, iridium, or rhodium catalyst, or a combination thereof. In another embodiment, the catalyst is a platinum group metal catalyst. For example, the catalyst may be a palladium or platinum catalyst. In yet another embodiment, preferably the catalyst is a palladium catalyst.

The catalyst may be supported on carbon, barium sulfate, alumina, strontium carbonate, calcium carbonate and the like. Thus, for example, catalysts include palladium on barium sulfate, palladium on carbon, palladium on alumina, palladium on strontium carbonate, palladium on barium carbonate, palladium on calcium carbonate, and the like. In a further embodiment of the invention, preferably the palladium catalysts are palladium on barium sulfate and palladium on carbon, particularly palladium on barium sulfate.

The halide used in the process may be a fluoride, chloride, bromide, or iodide ion. In one embodiment, preferably, the halide used in the process is chloride or bromide. In a further embodiment, preferably the halide is bromide.

The halide source may be any salt that does not interfere with the purification steps. For example, the halide source may be an alkali metal halide, alkaline earth metal halide, transition metal halide, halide salt of an organic cation, or the like. In one embodiment, the halide source is an alkali metal bromide, alkali metal chloride, alkaline earth metal bromide, alkaline earth metal chloride, transition metal bromide, transition metal chloride, bromide or chloride salt of an organic cation, or the like. In another embodiment, the halide source is a bromide salt where the cation does not interfere with the purification of the compounds of formulae 1A-7A. In one particular embodiment, the halide source is LiBr, NaBr, KBr, $MgBr_2$, $CaBr_2$ or $NH_4Br$. In yet a further embodiment, the halide source is LiBr or KBr.

In general, the strong acid or mixture of strong acids preferably has an approximate pKa (relative to water) of about −9 or less. In addition, after the starting material of Formulae 1-7, the strong acid, the halide, the catalyst and the solvent are charged In the reaction vessel, the reaction mixture preferably has a chloride or bromide concentration of about $2.1 \times 10^{-5}$ M to $1.8 \times 10^{-4}$ M or less. Experimental evidence to-date generally shows that a greater halide concentration negatively impacts the yield of the reaction. In one embodiment of the invention, the strong acid is sulfuric acid, perchloric acid or a mixture of sulfuric and perchloric acids. In a further embodiment, the strong acid, preferably, is sulfuric acid. Without being bound by theory, the addition of the strong acid and halide to the reaction is believed to act to prevent side reactions such as reduction of the carbon-nitrogen double bonds.

The process may advantageously be carried out in carboxylic acid or alcoholic solvents. For example, the solvent may be methanol, ethanol, n-propanol, formic acid, acetic acid, ethanoic acid, propionic acid, and the like, or mixtures thereof. In one embodiment, the solvent is a carboxylic acid. In a further embodiment, the solvent is acetic acid.

The hydrogen source for the hydrogenation reaction is preferably hydrogen gas. The gas pressure will typically fall within the range of about 1 to 4 atmospheres. In one embodiment, the pressure range is from about 1 to 3 atmospheres. In a further embodiment of the invention, the pressure range is from about 2.0 to 2.8 atmospheres.

The reaction temperature of the process is not narrowly critical and typically falls within the range of about 40-100° C., preferably of about 50-80° C., and most preferably of about 70-75° C.

Generally, any reaction vessel which can withstand the pressure, temperature and corrosive properties of the reaction mixture can be used to carry out the process of the invention.

In one embodiment, the final product is obtained by filtration using techniques known in the art. In another embodiment, the method of filtration is pouring the reaction product into water and adding 20% sodium hydroxide or ammonium hydroxide to a pH of about 7-8 and filtering to give the desired product.

Definitions

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denote optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "carboxylic acid" refers to a RC(O)OH compound where R can be hydrogen, or substituted or unsubstituted alkyl, alkenyl, alkynyl, aryl, substituted aryl. Exemplary carboxylic acids are formic acid, acetic acid, ethanoic acid, propionic acid, and the like.

The terms "halogen" or "halo" as used herein alone or as part of another group refer to chlorine, bromine, fluorine, and Iodine.

The term "halide" refers to fluoride, chloride, bromide, or iodide ions.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics such as furyl, pyridyl, oxazolyl, pyrrolyl, indolyl, quinolinyl, or isoquinolinyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, acyl, acyloxy, nitro, amino, amido, nitro, cyano, ketals, acetals, esters and ethers.

The term "precious metal catalyst" refers to a solid metal catalyst in whatever form suitable and effective for achieving the hydrogenation reactions of the instant invention. Exemplary and preferred precious metal catalysts include platinum, palladium, ruthenium, osmium, iridium, rhodium, and the like, or mixtures thereof.

The following examples illustrate the invention.

EXAMPLES

Generally, a stirred Parr reactor was used for reactions under hydrogen, unless a Parr shaker is mentioned. The stirring speed was the same in all experiments and was estimated to be around 300 RPM.

Example 1

Conversion of Alpha-hydroxy Zolpidem to Zolpidem Base

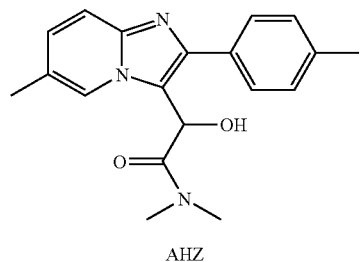

AHZ

Alpha hydroxy zolpidem (AHZ) was prepared by procedures similar to those in U.S. Pat. No. 4,794,185. Samples of this AHZ may have chloride ion in them, up to 0.5% by weight. The chloride ion has an effect on the reduction. Samples were washed with water until the chloride (as NaCl) concentration was as low as possible, in the region of 0.04% chloride by weight.

A solution of concentrated sulfuric acid (6.8 mL) diluted to 40 mL with glacial acetic acid was prepared (this was used for a number of experiments). A sample of low chloride AHZ, 1.50 g, was weighed out into the glass insert of a Parr stirred reactor (450 mL reactor volume). To this was added 37 mL of glacial acetic acid, followed by 3.0 mL of the sulfuric acid in acetic acid solution (containing 0.51 mL of concentrated sulfuric acid). The mixture was swirled until the solid dissolved. To this was added 25 µL of 1.4M LiBr in water. The mixture was swirled to assure mixing and to wash down any solid on the side of the glass. Then, 260 mg of 5% Pd/BaSO$_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 20-25 PSI of hydrogen and the stirrer was started at a medium speed. The system was heated to 70° C. and controlled using a thermocouple. When the reaction had reached 60-70° C., the system was adjusted to a pressure of 35 PSI of hydrogen. It was closed off from further hydrogen in a reaction on this scale. The reaction was run for 21 hours. In general, a few hours after no hydrogen pressure change was sufficient for essentially complete reaction. The mixture was allowed to cool to 20-40° C. The reactor was vented, filled with nitrogen and vented several times. The mixture was poured into a beaker. A total of 6 mL of glacial acetic acid was used in rinsing and transferring the mixture from the reactor to the beaker. The mixture was filtered through a Whatman (fiberglass) microfibre filter. The filtrate was poured into 80 mL of ice-cooled water, with stirring. Ammonium hydroxide, approximately 50 mL, was added slowly, to a pH>8. The mixture was stirred ten minutes and filtered. The solid was washed with water. This material was 98.2% zolpidem base by HPLC area purity. The yield was typically 90%.

Examples run by the above procedure are given in the table below. The reagents are all In the amounts described in Example 1, except for the bromide salt. Reagents of AR quality were used. The total amount of salt solution used is listed in the table. Products with purity of at least 69% were recrystallized from isopropanol, as in Example 1, to give zolpidem of >95% purity.

REDUCTIONS OF ALPHA-HYDROXY
ZOLPIDEM TO ZOLPIDEM BASE

| Example | Aqueous Bromide salt solution | Yield, % | Area Percent zolpidem in HPLC | Area Percent AHZ in HPLC | Reaction time, h |
|---|---|---|---|---|---|
| 1 | 25 µL of 1.4 M LiBr | 90 | 98.2 | 0.2 | 21 |
| 2 | 50 µL of 1.4 M LiBr | 90 | 95.3 | 0.6 | 6 |
| 3 | 15 µL of 1.4 M LiBr | 88 | 69.6 | 9.2 | 22 |
| 4 | 25 µL of 1.4 M NaBr | 91 | 92.3 | 1.6 | 5 |
| 5 | 35 µL of 1.4 M KBr | 91 | 98.5 | 0.4 | 6 |

Example 6

A solution of concentrated sulfuric acid (6.8 mL) diluted to 40 mL with glacial acetic acid was prepared. A sample of low chloride AHZ, 3.00 g, was weighed out. To this was added 37 mL of glacial acetic acid, followed by 6.0 mL of the sulfuric acid in acetic acid solution (contains 1.0 mL of concentrated sulfuric acid). The mixture was swirled until the solid dissolved. To the mixture was added 30 µL of 1.4M NaBr In water. The mixture was swirled to assure mixing and to wash down any solution on the side of the glass. Then, 267 mg of 5% Pd/BaSO$_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 20-25 PSI of hydrogen and the stirrer was started at a medium speed. The system was heated to 70° C. and controlled using a thermocouple. When the reaction had reached 60-70° C., the system was adjusted to a pressure of 30-35 PSI of hydrogen. It was closed off from further hydrogen in a reaction on this scale. The reaction was run at 70° C. at least until there was no further pressure change, in this case 17 hours. After the reaction, the mixture was allowed to cool to 20-40° C. The reactor was vented, filled with nitrogen and vented several times. The mixture was poured into a beaker. A total of 8 mL of glacial acetic acid was used in rinsing and transferring the mixture from the reactor to the beaker. The mixture was filtered through a Whatman microfibre filter. The filtrate was poured into 100 mL of ice cooled water, with stirring. Ammonium hydroxide, 55 mL, was added slowly, to a pH>8. The mixture was stirred ten minutes and filtered. The solid was washed with water. This material was 98.4% zolpidem base by HPLC area purity. The yield was 92%.

Example 7

A solution of concentrated sulfuric acid (6.8 mL) diluted to 40 mL with glacial acetic acid was prepared. A sample of low chloride AHZ, 4.50 g, was weighed out. To this was added 35 mL of glacial acetic acid, followed by 9.0 mL of the sulfuric acid in acetic acid solution (contains 1.5 mL of concentrated sulfuric acid). The mixture was swirled until the solid dissolved. To this was added 45 µL of 1.4M NaBr in water. The mixture was swirled to assure mixing and to wash down any solid on the side of the glass. Then, 400 mg of 5% Pd/BaSO$_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 25 PSI of hydrogen and the stirrer was started at a medium speed. The system was heated to 70° C. and controlled using a thermocouple. When the reaction reached 60-70° C., the system was adjusted to a pressure of 35 PSI of hydrogen. It was closed off from further hydrogen in a reaction on this scale. The reaction was run at 70° C. for 6 hours. After the reaction, the mixture was allowed to cool to 20-40° C. with stirring. The reactor was vented, filled with nitrogen and vented several times. The mixture was poured into a beaker. A total of 10 mL of glacial acetic acid was used in rinsing and transferring. The mixture was filtered through a Whatman microfibre filter. The filtrate was poured into 130 mL of ice-cooled water with stirring. Ammonium hydroxide, 60 mL, was added slowly to a pH>8. The mixture was stirred ten minutes and filtered. The solid was washed with water. This material was 88.9% zolpidem base by HPLC area purity, and contained some unreacted AHZ (4.8%). The yield was 97%.

Example 8

Recrystallization of Crude Zolpidem

Some samples were quite pure as a crude product, but some were only around 70% pure; both types were recrystallized from isopropanol.

A 5.9 g sample of crude zolpidem base of 73% purity (the Impurities were mainly AHZ and AHZ-O-Acetate) was recrystallized from 40 mL of isopropanol, stirring it while allowing to cool. Filtration gave 2.7 g of zolpidem, 98.4% purity by HPLC area.

A 2.56 g sample of zolpidem base (95% purity) was recrystallized from 14 mL of isopropanol to give 2.02 g (80% recovery) of zolpidem, 97.6% purity.

A 14.4 g sample of zolpidem (97% purity by HPLC area) was recrystallized from 86 mL of isopropanol. The mixture was allowed to cool with stirring to room temperature and filtered. The filtrate was used to wash the remaining solid from the flask. The filter cake was washed with 7 mL of isopropanol to give 10.3 g of a white solid, 99.2% zolpidem by HPLC area (254 nM UV detector).

Example 9

α-hydroxy-zolpidem-O-acetate

The O-Acetate of AHZ was produced along with the zolpidem product during the course of the above hydrogenations (Examples 1-7), and can be detected in the product in small amounts. Simply heating AHZ in glacial acetic acid with the typical amount of sulfuric acid present will convert most of it to the acetate in a few hours at 70° C. However, to obtain a clean sample for Example 10, the procedure below was followed.

A mixture of 3.00 g of AHZ, 1.50 mL of triethylamine, 15 mL of dichloromethane and 130 mg of 4-dimethylaminopyridine was stirred in an ice bath. Acetyl chloride, 0.75 mL was added and the mixture stirred overnight under nitrogen, letting the ice melt and the reaction come to room temperature. Then, 50 mL of dichloromethane was added followed by 5 mL of 1 M NaOH. The pH was >11. The mixture was separated and the dichloromethane dried with magnesium sulfate. The dichloromethane was evaporated and the residue stirred with 80 mL ethyl acetate. The ethyl acetate was washed twice with 20 mL of water, dried over magnesium sulfate, evaporated and left under high vacuum for a few hours to give 2.6 g of the desired product. The NMR (300 MHz, $CDCl_3$) shows aromatic peaks at δ values of 8.47 (broad, 1H), 7.56 (m, 3H), 7.28 (m, 2H), 6.83(s, 1H) as well as methyl peaks from 2.3-2.9 (15H total), with the acetate $CH_3$ at δ 2.3.

Example 10

Zolpidem

A 1.57 g sample of the O-acetate from Example 9 was dissolved in 37 mL of glacial acetic acid and to this was added 0.5 mL of sulfuric acid (3 mL of acetic acid solution) followed by 25 µL of 1.4 NaBr solution (aqueous) and 263 mg of 5% $Pd/BaSO_4$. The hydrogenation was run at a pressure of 30-40 PSI in the usual manner for 7 hours. Hydrogen was added, as needed, when the pressure was closer to 30 PSI. Work-up In the usual manner gave 1.13 g (86% yield). HPLC analysis indicated 74.4% zolpidem, 15.6% of starting material and 4.7% of AHZ. The crude product was recrystallized from isopropanol to give zolpidem.

Example 11

α-hydroxy-zolpidem-O-propionate

A mixture of 4.00 g of AHZ, 2.08 mL of triethylamine, 20 mL of dichloromethane and 185 mg of 4-dimethylaminopyridine was stirred in an ice bath. Propionyl chloride, 1.20 mL, was added and the mixture stirred overnight under nitrogen, letting the ice melt and the reaction come to room temperature. Then, 5 mL water was added followed by 0.5 mL of 1 M NaOH. The pH was 8.2. The mixture was separated and the dichloromethane solution concentrated on a rotary evaporator. The residue was stirred with 40 mL ethyl acetate and 15 mL of water. The ethyl acetate was separated, dried over magnesium sulfate and evaporated on a rotary evaporator to a solid. It was left under high vacuum for a few hours to give 4.2 g of the desired product.

NMR (300 MHz, $CDCl_3$): δ 8.5(s, 1H), 7.5-7.6(m, 3H), 7.29(d, 1H), 7.13(dd, 1H), 2.81(s, 3H), 2.6(m, geminal coupling, 2H), 2.46(s, 3H), 2.40(s, 3H), 2.37(s, 3H), 1.27(t, 3H)

Example 12

Zolpidem

A 1.66 g sample of the O-propionate from Example 11 was dissolved in 40 mL of glacial acetic acid and to this was added 0.5 mL of sulfuric acid (3 mL of acetic acid solution) followed by 35 µL of 1.4M NaBr solution (aqueous) and 262 mg of 5% $Pd/BaSO_4$. The hydrogenation was run at a pressure of 30-40 PSI In the usual manner for 12.5 hours. Hydrogen was maintained at a pressure of 30-40 PSI by adding it from the cylinder periodically. Work-up in the usual manner gave 1.32 g (97% yield). HPLC analysis indicated 95.3% zolpidem, 0.8% of starting material and 1.0% of AHZ, as well as other peaks. The crude product was recrystallized from isopropanol to give zolpidem.

Example 13

Zolpidem

A solution of concentrated sulfuric acid (6.8 mL) diluted to 40 mL with glacial acetic acid was prepared. A sample of low chloride AHZ, 7.5 g, was weighed out. To this was added 30 mL of glacial acetic acid, followed by 15 mL of the sulfuric acid in acetic acid solution (contains 2.5 mL of concentrated sulfuric acid). The mixture was swirled until the solid dissolved. To this was added 54 µL of 1.4M NaBr in water. The mixture was swirled to assure mixing and to wash down any solid on the side of the glass. Then, 406 mg of 5% $Pd/BaSO_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 25 PSI of hydrogen and the stirrer was started at a medium speed. The system was heated to 70° C. and controlled using a thermocouple. When the reaction has reached 60-70° C., the system was adjusted to a pressure of 37 PSI of hydrogen. The hydrogen valve was closed and hydrogen was added periodically to maintain a pressure of 30-40 PSI. The reaction was run at 70° C. for 14 hours. After the reaction, the mixture was allowed to cool to 31° C. with stirring. The reactor was vented, filled with nitrogen and vented several times. The mixture was poured into a beaker. A total of 10 mL of glacial acetic acid was used in rinsing and transferring the mixture from the reactor into the beaker. The mixture was filtered through a Whatman microfibre filter. The filtrate was poured into 150 mL of ice-cooled water, with stirring, followed by a rinse of the flask with 20 mL of water into the same. The pH was 1.1. During the pH adjustment, 50 mL of water was added to help stir the initially thick mixture. Ammonium hydroxide, 70 mL, was added slowly, to a pH>9. The mixture was stirred 20 minutes and filtered. The solid was washed with water. This material was 98.3% zolpidem base by HPLC area purity. The yield was 87%.

Example 14

Zolpidem

A solution of concentrated sulfuric acid (6.8 mL) diluted to 40 mL with glacial acetic acid was prepared. A sample of low chloride AHZ, 9.0 g, was weighed out. To this was added 30 mL of glacial acetic acid, followed by 15 mL of the sulfuric acid in acetic acid solution (contained 2.5 mL of concentrated sulfuric acid), To this was added 65 µL of 1.4M NaBr in water. The mixture was swirled to assure mixing and to wash down any solid on the side of the glass. Then, 481 mg of 5% $Pd/BaSO_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 25 PSI of hydrogen and the stirrer was started at a medium speed. The system was heated to 70° C. and controlled using a thermocouple. When the reaction has reached 70° C., the system was maintained at a pressure of 30-40 PSI of hydrogen. The reaction was run at 70° C. for 14 hours. After the reaction, the mixture was allowed to cool to 31° C. with stirring. The reactor was vented, filled with nitrogen and vented several times. The mixture was poured into a beaker. A total of 10 mL of glacial acetic acid was used in rinsing and transferring the mixture from the reactor to the beaker. The mixture was filtered through a Whatman microfibre filter. The rest of the work-up was as in example 13. The product, a 91% yield, was 95.0% pure by HPLC.

Example 15

Zolpidem

A solution of concentrated sulfuric acid (6.8 mL) diluted to 40 mL with glacial acetic acid was prepared. A sample of low chloride AHZ, 9.0 g, was weighed out. To this was added 30 mL of glacial acetic acid, followed by 18 mL of the sulfuric acid in acetic acid solution (contained 3.0 mL of concentrated sulfuric acid). To this was added 65 μL of 1.4M NaBr in water. The mixture was swirled to assure mixing and to wash down any solid on the side of the glass. Then, 483 mg of 5% Pd/BaSO$_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 25 PSI of hydrogen and the stirrer was started at a medium speed. The system was heated to 70° C. and controlled using a thermocouple. When the reaction has reached 70° C., the system was maintained at a pressure of 30-40 PSI of hydrogen. The reaction was run at 70° C. for 14 hours. After the reaction, the mixture was allowed to cool to 31° C. with stirring. The reactor was vented, filled with nitrogen and vented several times. The mixture was poured into a beaker. A total of 10 mL of glacial acetic acid was used in rinsing and transferring the mixture from the reactor to the beaker. The mixture was filtered through a Whatman microfibre filter. The rest of the work-up was as in example 13. The product, a 91% yield, was 97.8% pure by HPLC.

Example 16

A 1.00 g sample of AHZ was dissolved in 25 mL of AcOH. Sulfuric acid, 0.34 mL, in acetic acid (1 mL of solution) was added, followed by 50 μL of 1.4M aqueous NaCl solution and 175 mg of 5% Pd/BaSO$_4$. Hydrogenation was run at 70° C. and a pressure of 20 PSI in a Parr Shaker apparatus for 4.5 hours. Filtration and aqueous work-up to a basic pH gave the crude product. HPLC of this Indicated 36% of the product to be zolpidem.

Example 17

A 1.00 g sample of AHZ was dissolved in 25 mL of AcOH. Sulfuric acid, 0.34 mL, in acetic acid (1 mL of solution) was added, followed by 4.0 mg of choline chloride (Aldrich) and 170 mg of 5% Pd/BaSO$_4$. Hydrogenation was run at 70° C. and a pressure of 20-30 PSI in a Parr Shaker apparatus for four hours. Filtration and aqueous work-up to a basic pH gave the crude product, 0.87 g. HPLC of the crude product indicated 64% of the product to be zolpidem.

Example 18

A sample of AHZ, 1.50 g, was weighed out. To this was added 45 mL of glacial acetic acid, followed by 2.01 g of 70% ACS perchloric acid and 35 μL of 1.4M NaBr in water. The mixture was swirled to assure mixing and to wash down any solid on the side of the glass. Then, 260 mg of 5% Pd/BaSO$_4$ catalyst (Engelhard) was added. The reactor was closed and placed in a heating mantle. Through the appropriate valves, the system was filled with nitrogen and vented several times. Hydrogen was added and kept at a pressure of 15-20 PSI. The system was heated to 70° C. and controlled using a thermocouple. The reaction was run for 5 hours. Aqueous work-up with ammonia yielded a gum. Extraction with dichloromethane gave the crude product. HPLC indicated that 35% of the product was zolpidem base.

Example 19

A 1.00 g sample of AHZ was dissolved in 25 mL of AcOH. Sulfuric acid, 0.34 mL, in acetic acid (1 mL of solution) was added, followed by 25 μL of 0.95M aqueous NaF solution and 175 mg of 5% Pd/BaSO$_4$. Hydrogenation was run at 70° C. and a pressure of 20-30 PSI in a Parr Shaker apparatus for five hours. Filtration and aqueous work-up to a basic pH gave the crude product, a gum. HPLC of this indicated 29% of the product to be zolpidem. Also present were AHZ, 23%, and AHZ-C-Acetate, 34%.

Example 20

A 3.00 g sample of AHZ was dissolved in 40 mL of 96% formic acid. Sulfuric acid, 1.86 g, was added, followed by 30 μL of 1.4M aqueous NaBr solution and 268 mg of 5% Pd/BaSO4. The hydrogenation was run at 70° C. and a pressure of 30-40 PSI for 5 hours. The mixture was filtered and washed with 4 mL of formic acid. The filtrate was poured into 120 mL of water followed by a 20 mL water rinse. Ammonium hydroxide was added to a pH above 8. The mixture was extracted with 100 mL dichloromethane followed by 50 mL more dichloromethane. The dichloromethane was separated and evaporated to give an oil, which solidified to 2.59 g. HPLC analysis indicated 78% of zolpidem base and 18% of AHZ.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in limiting sense.

What is claimed is:

1. A process for the preparation of a heteroaryl acetamide from a heteroaryl α-hydroxyacetamide, the process comprising directly hydrogenating the heteroaryl α-hydroxyacetamide in the presence of a strong acid, a halide, and a precious metal catalyst, the heteroaryl α-hydroxyacetamide having the structure of Formula 1 and the heteroaryl acetamide has the structure of Formula 1A:

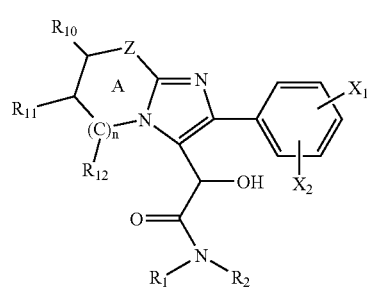

-continued

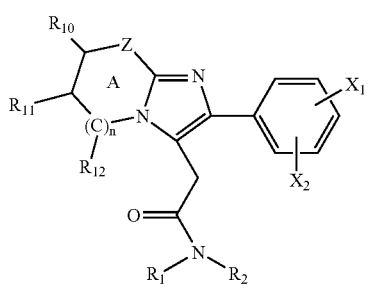

wherein
Z is O, $NR_{20}$ or $CR_{21}$;
$X_1$ and $X_2$ are independently selected from the group consisting of hydrogen, halogen, $C_{1-4}$ alkoxy, $C_{1-6}$ alkyl, $-CF_3$ and $CH_3SO_2-$;
$R_1$ and $R_2$ are independently hydrogen or hydrocarbyl;
$R_{10}$ is hydrogen, halogen, $C_{1-4}$ alkyl, or a member of a fused ring wherein the fused ring is (i) a substituted or unsubstituted, saturated or unsaturated, five or six-membered, hyeterocyclic or carbocyclic ring fused to the A ring comprising $R_{10}$, the carbon atom to which $R_{10}$ is attached, $R_{20}$, and the nitrogen atom to which $R_{20}$ is attached, or (ii) a six-membered, aromatic, carbocyclic ring fused to the A ring comprising $R_{10}$, $R_{11}$, and the carbon atoms to which $R_{10}$ and $R_{11}$ are attached, optionally substituted with Y at a substitutable position thereof;
$R_{11}$ is hydrogen, halogen, $C_{1-4}$ alkyl, or a member of a fused ring wherein the fused ring is (i) a six-membered, aromatic, carbocyclic ring fused to the A ring comprising $R_{10}$, $R_{11}$, and the carbon atoms to which $R_{10}$ and $R_{11}$ are attached, optionally substituted with Y at a substitutable position thereof, or (ii) a six-membered, aromatic, carbocyclic ring fused to the A ring comprising $R_{11}$, $R_{12}$, and the carbon atoms to which $R_{11}$ and $R_{12}$ are attached, optionally substituted with Y at a substitutable position thereof;
$R_{12}$, if present, is hydrogen, halogen, $C_{1-4}$ alkyl, or a member of a fused ring wherein the fused ring is (i) a six-membered, aromatic, carbocyclic ring fused to the A ring comprising $R_{11}$, $R_{12}$, and the carbon atoms to which $R_{11}$ and $R_{12}$ are attached, optionally substituted with Y at a substitutable position thereof;
$R_{20}$ is $C_{1-5}$ alkyl or a member of a fused ring wherein the fused ring is a substituted or unsubstituted, saturated or unsaturated, five or six-membered, heterocyclic or carbocyclic ring fused to the A ring comprising $R_{10}$, the carbon atom to which $R_{10}$ is attached, $R_{20}$, and the nitrogen atom to which $R_{20}$ is attached;
$R_{21}$ is hydrogen, halogen or $C_{1-4}$ alkyl;
n is 0 or 1;
each Y is independently hydrogen, halogen or $C_{1-4}$ alkyl; and
when Z is $CR_{21}$, the A ring is aromatic.

2. The process of claim 1 wherein $X_1$ and $X_2$ are independently selected from the group consisting of hydrogen, halogen, $C_{1-4}$ alkoxy and $C_{1-6}$ alkyl, $R_1$ and $R_2$ are independently hydrogen or $C_{1-5}$ alkyl and Y is hydrogen, halogen or $C_{1-4}$ alkyl.

3. A process for the preparation of an imidazopyridine acetamide from an imidazolpyridine α-hydroxyacetamide, the process comprising directly hydrogenating the imidazopyridine α-hydroxyacetamide in the presence of a strong acid, a halide, and a precious metal catalyst, the imidazopyridine α-hydroxyacetamide has the structure of Formula 6 and the imidazopyridine acetamide has the structure of Formula 6A:

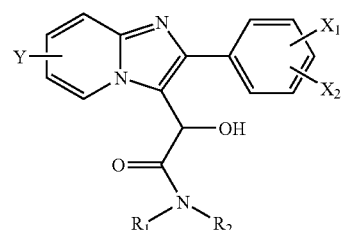

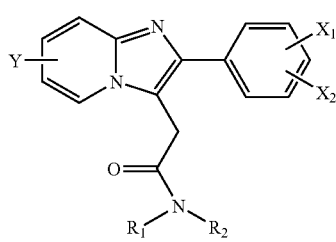

wherein
Y is hydrogen, halogen or $C_{1-4}$ alkyl;
$X_1$ and $X_2$ are independently selected from the group consisting of hydrogen, halogen, $C_{1-4}$ alkoxy, $C_{1-6}$ alkyl, $-CF_3$ and $CH_3SO_2-$; and
$R_1$ and $R_2$ are independently hydrogen or $C_{1-5}$ alkyl.

4. The process of claim 3 wherein Y is methyl, $X_1$ and $X_2$ are independently hydrogen or methyl and $R_1$ and $R_2$ are methyl.

5. The process of claim 3 wherein the strong acid is sulfuric acid.

6. The process of claim 3 wherein the halide is a bromide ion.

7. The process of claim 3 wherein the precious metal catalyst is a palladium catalyst.

8. The process of claim 7 wherein the precious metal catalyst is palladium on barium sulfate.

9. A process for the preparation of an imidazopyridine acetamide from an imidazopyridine α-hydroxyacetamide, the process comprising directly hydrogenating an imidazopyridine α-hydroxyacetamide in the presence of hydrogen gas, a strong acid or mixture of strong acids with a pKa of about −9 or less, a chloride or bromide ion and a palladium catalyst, wherein the imidazopyridine α-hydroxyacetamide has the structure of Formula 7 and the imidazopyridine acetamide product has the structure of Formula 7A:

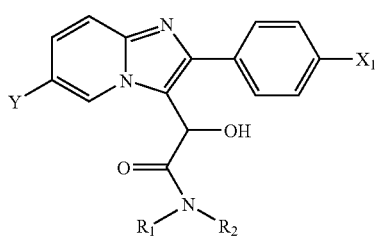

-continued

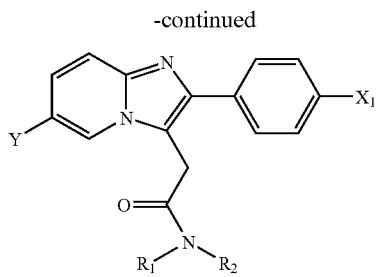

7A wherein
Y is $C_{1-4}$ alkyl;
$X_1$ $C_{1-4}$ alkyl; and
$R_1$ and $R_2$ are independently hydrogen or $C_{1-5}$ alkyl.

10. The process of claim 9 wherein Y, $X_1$, $R_1$ and $R_2$ are methyl.

11. The process of claim 9 wherein the bromide or chloride ion is a bromide ion.

12. The process of claim 9 wherein the palladium catalyst is palladium on barium sulfate.

13. The process of claim 9 wherein the imidazopyridine α-hydroxyacetamide, the strong acid, the chloride or bromide ion and the palladium catalyst is dissolved in a solvent of methanol, ethanol, n-propanol, formic acid, acetic acid, ethanoic acid or propionic acid.

14. The process of claim 13 wherein the solvent is acetic acid.

15. The process of claim 9 wherein the reaction temperature is about 70° C. to about 75° C.

16. The process of claim 9 wherein the reaction pressure is about 2.0 atmospheres to about 2.8 atmospheres.

17. The process of claim 10 wherein the strong acid is sulfuric acid, the bromide or chloride ion is bromide ion and the catalyst is palladium on barium sulfate.

18. The process of claim 9 wherein the strong acid is sulfuric acid, the bromide or chloride ion is bromide ion and the catalyst is palladium on barium sulfate.

19. The process of claim 18 wherein the reaction temperature is about 70° C. to about 75° C. and the reaction pressure is about 2.0 atmospheres to about 2.8 atmospheres.

20. The process of claim 1, wherein the process further comprises directly hydrogenating the heteroaryl α-hydroxyacetamide in the presence of hydrogen gas, in addition to the strong acid, the halide, and the precious metal catalyst.

21. The process of claim 3, wherein the process further comprises directly hydrogenating the imidazolpyridine α-hydroxyacetamide in the presence of hydrogen gas, in addition to the strong acid, the halide, and the precious metal catalyst.

* * * * *